United States Patent [19]
Griffith et al.

[11] Patent Number: 5,793,205
[45] Date of Patent: Aug. 11, 1998

[54] COIL AND GUIDE SYSTEM FOR EDDY CURRENT EXAMINATION OF PIPE

[75] Inventors: John C. Griffith; Barry L. Everett; Randall G. Krotke, all of Lynchburg; William S. Cooper, Forest, all of Va.

[73] Assignee: Framatome Technologies, Inc., Lynchburg, Va.

[21] Appl. No.: 616,150

[22] Filed: Mar. 14, 1996

[51] Int. Cl.$^6$ .................... G01N 27/82; G01R 33/00
[52] U.S. Cl. .................... 324/238; 324/240; 324/262; 324/243
[58] Field of Search .................... 324/228, 237, 324/238, 239, 240, 241, 242, 243, 260, 262, 234

[56] References Cited

U.S. PATENT DOCUMENTS

| | | | |
|---|---|---|---|
| 2,575,811 | 11/1951 | Hofammann et al. | 324/262 |
| 4,596,953 | 6/1986 | Nagasaka et al. | 324/242 |
| 4,629,991 | 12/1986 | Wheeler | 324/232 |
| 4,644,272 | 2/1987 | Janos | 324/240 |
| 4,673,879 | 6/1987 | Harris et al. | 324/240 |
| 4,785,243 | 11/1988 | Abramczyk et al. | 324/232 |
| 4,855,678 | 8/1989 | Kreiskorte | 324/262 |
| 4,862,079 | 8/1989 | Chickering et al. | 324/227 |
| 5,103,172 | 4/1992 | Stoll | 324/226 |
| 5,279,160 | 1/1994 | Koch | 73/643 |
| 5,291,136 | 3/1994 | Van der Veer et al. | 324/262 |
| 5,402,066 | 3/1995 | Hickman, Jr. et al. | 324/242 |
| 5,434,506 | 7/1995 | Flora | 324/242 |
| 5,453,688 | 9/1995 | Cecco et al. | 324/220 |
| 5,581,037 | 12/1996 | Kwun et al. | 324/242 |

FOREIGN PATENT DOCUMENTS 1415161  8/1988  U.S.S.R. .................... 324/238

*Primary Examiner*—Sandra L. O'Shea
*Assistant Examiner*—Jay M. Patidar
*Attorney, Agent, or Firm*—Rhodes Coats & Bennett, L.L.P.

[57] ABSTRACT

An eddy current testing apparatus for nondestructive examination of pipe. The apparatus includes an eddy current coil adapted to removably circumferentially surround the pipe, the coil including a cable having a plurality of conductors adapted to form a continuous conductor coil when the cable is circumferentially wrapped around the pipe. A guide system extends along the length and adjacent to the surface of the pipe and a coil form is adapted to removably circumferentially surround the pipe and engage the guide system to provide for travel of the coil along the pipe.

52 Claims, 7 Drawing Sheets

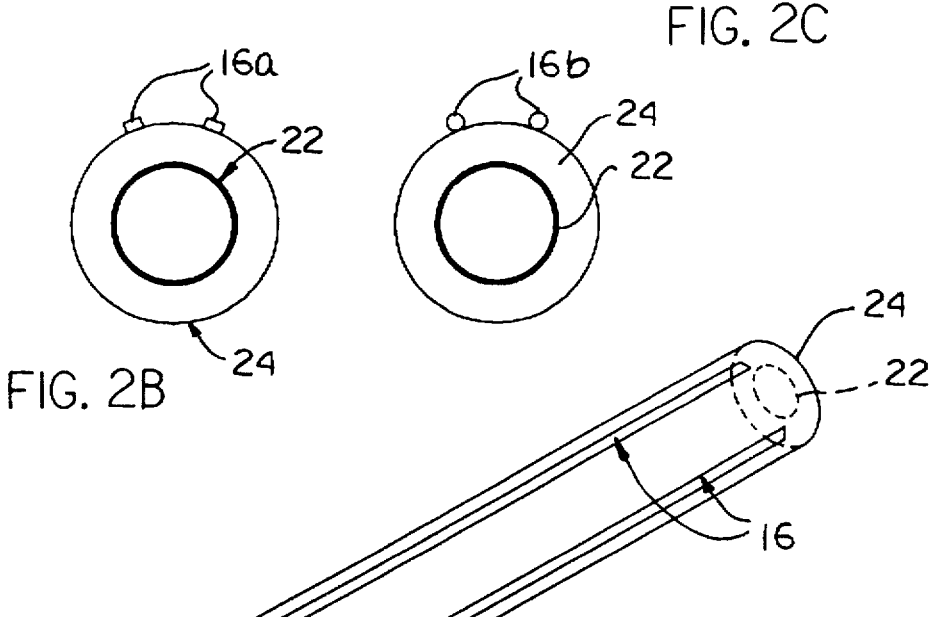
FIG. 2C
FIG. 2B
FIG. 2A
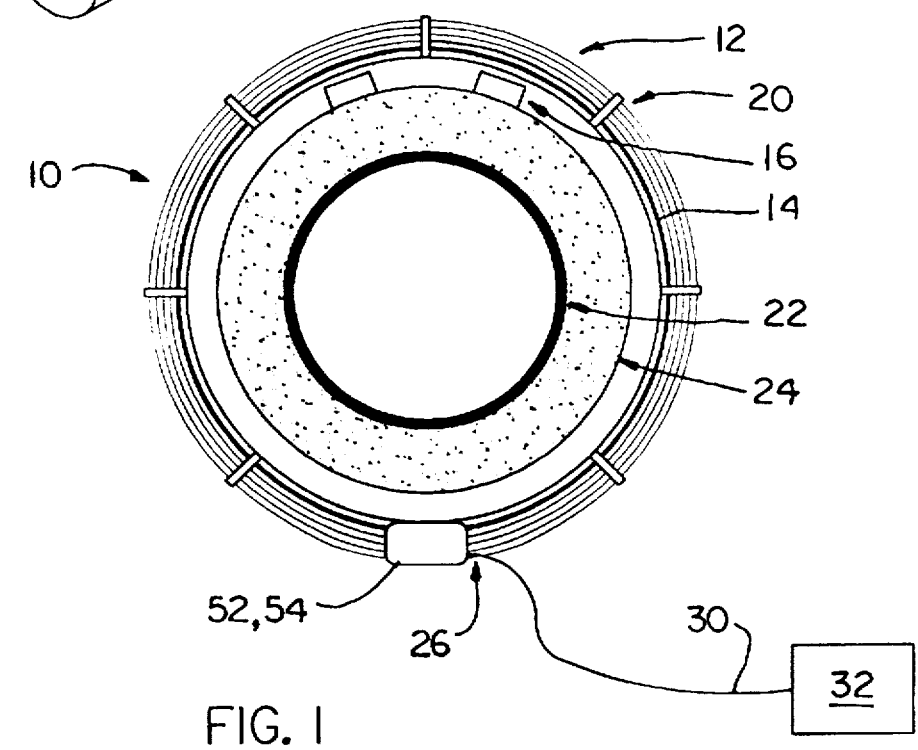
FIG. 1

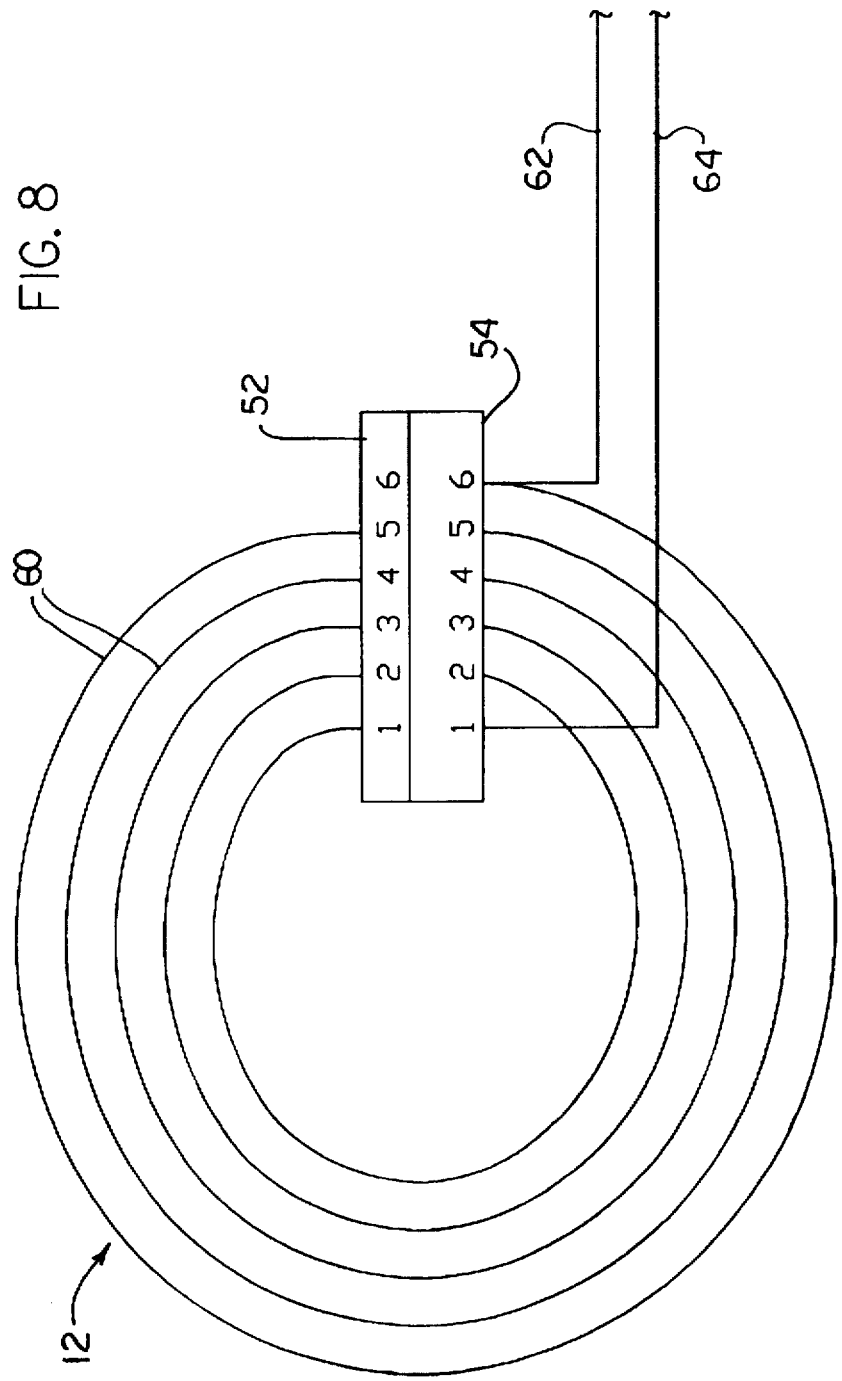

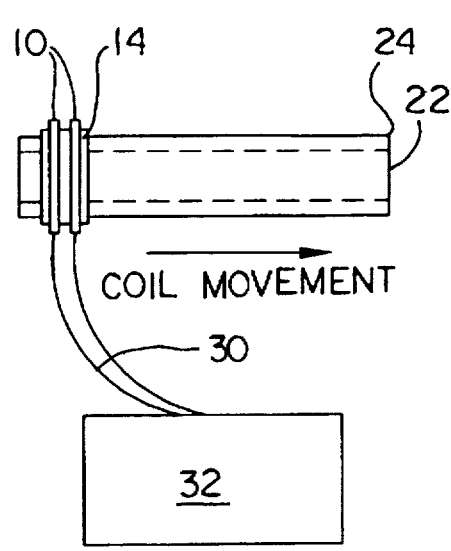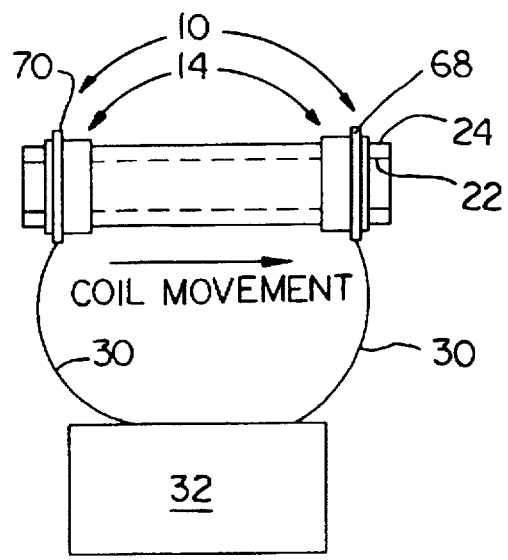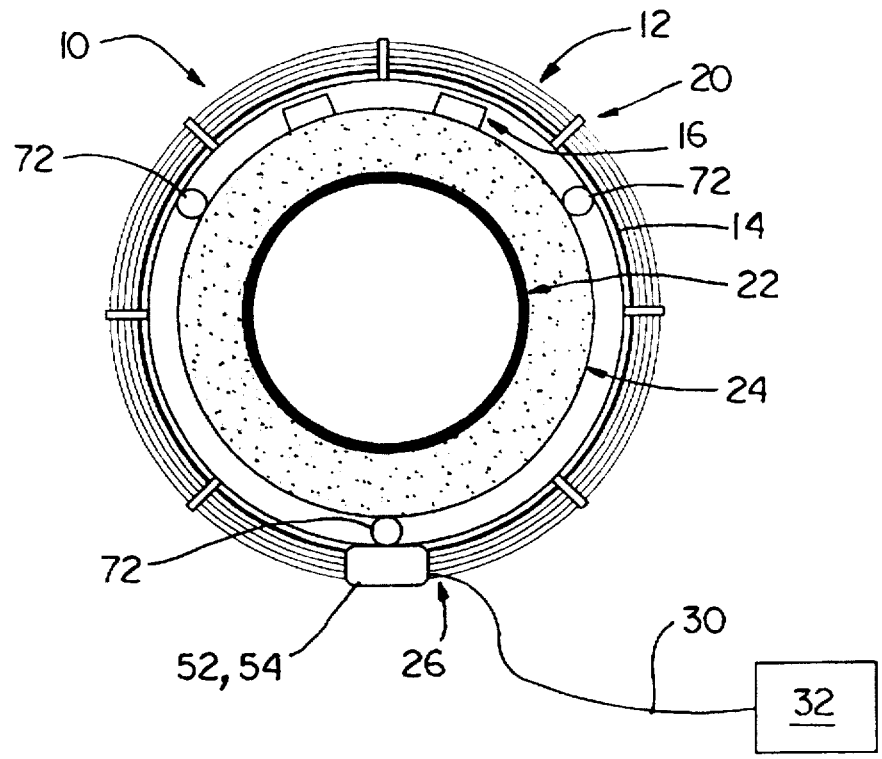

COIL AND GUIDE SYSTEM FOR EDDY CURRENT EXAMINATION OF PIPE

BACKGROUND OF THE INVENTION (1) Field of the Invention

The present invention relates generally to nondestructive examination (NDE) systems and, more particularly, to a system for more efficiently examining installed and/or insulated piping systems for degradation from corrosion, erosion, fatigue, pitting and wear.

(2) Description of the Prior Art

Operational piping systems are subject to a number of factors leading to degradation of pipe integrity. Among these degradational effects are corrosion, erosion, fatigue, pitting and wear. NDE of piping systems is essential in cases where a failure of the system could damage equipment, contaminate the environment or injure personnel. The presence of insulation surrounding the outside of the pipe has previously made NDE extremely difficult and costly.

Methods commonly used for the examination of such piping systems are quite varied. These methods include, among others, ultrasonic testing (UT), radiography, x-ray examination, dye penetrant testing, visual examination and eddy current testing. Each method has significant disadvantages.

UT is one of the more common methods of examining pipe from the outside. Unfortunately, this examination is at least partially destructive since UT requires removal of the pipe insulation in order to allow the ultrasonic energy to couple with and into the wall of the pipe being examined. In many instances, the system using the pipe under examination must be secured, shut down, cooled and possibly drained to provide accurate testing results. Typically, prior to the UT examination, the pipe surface must be cleaned for good results.

The UT is typically performed by manually scanning locations on the pipe having a high potential for degradation in a grid-like pattern. Some examinations, using UT, are performed with a mechanical fixture programmed to scan the examination grid. In any case, UT is a very slow process. Thus, the speed of the UT limits applications to a relatively small percentage of the piping system. Otherwise, the primary system utilizing the piping system must be shut down for an inordinate amount of time. Furthermore, corrosion along the outside diameter of the pipe is difficult to examine with UT methods.

Radiography and x-ray examination typically require system draining and the use of expensive and potentially hazardous equipment. These methods usually do not require insulation removal or extensive surface preparation; however, such methods are not adequately sensitive to small volume cracking. In addition to the hazardous nature of such testing methods, access to areas surrounding the inspection zone must be restricted and examination times for these methods are often quite significant.

Dye penetrant examination methods also require insulation removal and pipe surface preparation. Typically, the system must be cooled to near ambient temperature for such examinations. In contrast with UT, dye penetrant methods cannot detect inside diameter pipe corrosion or erosion and are limited to cracking extending to the outside diameter pipe surface. Furthermore, the dye penetrant methods are unable to quantitatively measure the extent or depth of cracks present in the pipe. These methods require significant time for surface preparation, application of dye and developer, and subsequent visual examination.

Visual examination also requires the removal of insulation from the pipe. While visual examination methods may not require system draining or shut down, they often require significant surface cleaning. Furthermore, detection of degradation is limited to the outside diameter pipe surface. Additional methods must be used to quantify the degradation.

Presently available eddy current testing methods also have significant drawbacks. Pulsed eddy current techniques are designed to work with pipe insulation in place. They are most sensitive to pipe wall loss and may detect cracking if oriented properly. Most of these techniques use a small area coil which is manually or mechanically scanned over a grid pattern similar to the UT technique. The scanning methods, unfortunately, require a significant amount of time for examination.

The pulse techniques have an undesirable sensitivity to liftoff variations caused by nonuniform travel or movement of the eddy current coil. Certain pulsed eddy current applications provide accurate wall thickness measurements over large areas of pipe, which is valuable for general uniform pipe wall corrosion detection. However, these methods are of little use in detecting pitting or erosion damage. Additionally, these techniques require 1 to 10 seconds per reading at each grid location; therefore, resulting in extensive examination times.

NDE methods using a driver-pickup, pancake coil provide many of the features of the pulsed eddy current system while reducing examination sensitivity to liftoff variations. However, recent testing of such systems using the driver pickup pancake coil has shown a large sensitivity loss as insulation thickness increases.

U.S. Pat. No. 5,434,506, issued to Flora, discloses an eddy current inspection device for detecting defects located on a covered material, such as pipes. The defects are detected through eddy current inspection using stationary magnetic fields and scanning sensor arrays. A magnetizing yoke is held fixed to the cover of the component and a magnetic flux sensor is used to scan the area between the legs of the yoke over the cover of the component. Additionally, a fixed array of sensors may be provided between the legs of the yoke for automatic multiplexing of the sensors and sampling in sequence of signal responses picked up by sensors in the sensor array. An attachment means may be used for holding the yoke and sensor arrangement stationary with respect to the surface of a component during sampling of the signal responses.

U.S. Pat. No. 4,855,678, issued to Kreiskorte, discloses a device by which a sensor holder of a surface testing apparatus is moved along a preselected path of movement over the surface being examined. The device has a guide rail establishing the path of movement. The path of movement emulates the contour of the surface of the item being examined. The device is directed towards surface testing substantially flat surfaces, such as flat slabs.

U.S. Pat. No. 5,279,160, issued to Koch, discloses an array for NDE of cylindrical work pieces. The device has at least one supporting means serving to guide the work piece.

U.S. Pat. No. 5,402,066, issued to Hickman, Jr. et al., discloses a magnetic interferometer for performing nondestructive magnetic induction testing in inspection of wire rope and cable. The device concentrically surrounds a wire rope or cable to be tested and includes means for inducing a magnetic field in the rope or cable as well as means for detecting flux changes in the induced magnetic field. By detecting flux changes in the magnetic field, the condition of the rope or cable can be determined.

U.S. Pat. No. 4,673,879, issued to Harris et al., discloses an eddy current flaw detector having a rotatable field defining sleeve for selectively enhancing induced eddy currents in a work piece. The method and apparatus disclosed scans a generally cylindrical work piece for flaws. A cylindrical metallic sleeve is rotatably supported about a work piece path of travel. Two differentially wound energization coils surround the sleeve near two apertures in the sleeve. The coils are energized with a high-frequency signal that induces eddy currents in the work piece. The apertures periodically disrupt the eddy current inducing magnetic fields and enhance the signals from the coils indicative of the presence of flaws in the work piece.

U.S. Pat. No. 4,629,991, issued to Wheeler, discloses a tubing trip tool for use in determining the extent of defects in tubular sections of a continuous tubing string used in subterranean oil and gas wells. The tubing trip tool is mounted on a surface rig surrounding the tubing string and defects are magnetically detected during tubing removal from the well bore. The tool comprises a segmented expandable detector head(containing elements for measuring average wall thickness and local and axially extending defects. The expandable head is spring loaded and pneumatically actuated. Coupling detectors are located on the ends of the head to count tubing sections and to detect the presence of obstructions on the tubing to prevent damage to the detector head.

U.S. Pat. No. 4,862,079, issued to Chickering et al., discloses a device for locating and measuring wear in nuclear reactor control rods. Circumferential and radial eddy current test probes produce outputs corresponding respectively to volume and thickness of the control rod. A method is disclosed to determine cladding wear when the volume and thickness varies beyond preselected limits.

Thus, there remains a need for a new and improved NDE eddy current inspection system which does not require insulation removal or surface preparation and, at the same time, is capable of operating on a system without draining, shutting down or cooling down the system or pipes under examination thereby significantly reducing the amount of time for setup and examination of each pipe section. A system also is needed that provides a complete examination in a single pass of the examination device instead of time consuming grid scanning and provides sensitivity to small area wall loss on the inside diameter and outside diameter of the pipe for various piping system materials and insulation thicknesses and is sensitive to axially oriented cracking.

SUMMARY OF THE INVENTION

The present invention is directed to a nondestructive examination method for pipe examination using eddy currents. The invention includes a removable encircling coil which is wrapped in place on an installed and/or insulated and operating piping system to accommodate different pipe diameters and insulation (or lagging) thickness and ease the burden of wrapping the coil around the pipe. The coil is formed from a multiple conductor wire bundle having two ends. The two ends of the wire bundle are connected in a manner in which each conductor connects to the opposite end of an adjacent conductor, thereby forming a continuous single loop of conductors. The number of coil windings is the product of the number of conductors in the wire bundle and the number of times the wire bundle is wrapped around the coil form.

The present invention provides for quickly installing an absolute or differential bobbin type eddy current coil around an installed and/or insulated pipe without cutting the pipe. The encircling coil system of the present invention is cost effective and easily and efficiently installed and removed to facilitate data acquisition on accessible sections of pipe and quickly removed and reinstalled on a next section of pipe.

In the preferred embodiment, the invention also includes either a rail configuration and a flexible adjustable coil form. The rail configuration typically includes a set of thin rails installed along the longitudinal axis of the pipe being examined. The rails are installed on the outside of the uninsulated pipe or on the surface of the insulation of an insulated pipe and provide a smooth track for eddy current coil travel. The rails minimize liftoff variation or wobble movement of the eddy current coil during examination, thereby minimizing eddy current signal noise. The configuration of the rails or movement fixtures vary according to the geometry of the pipe being examined.

After the rails are installed on the pipe section being examined, a flexible coil form is placed around the pipe and rails. The coil form is adjusted to a diameter allowing smooth travel over the examination region. Once the coil form is in place, a coil winding is wrapped around the coil form to form an eddy current coil.

In an alternative embodiment, a movement fixture may used to provide a path of travel for the coil and coil form. Specifically, a mechanical pivot fixture may be used for providing non-linear travel of the coil along bends in the piping system being examined.

Accordingly, one aspect of the present invention is to provide an eddy current testing apparatus for nondestructive examination of pipe. The apparatus includes: (a) an eddy current coil adapted to removably circumferentially surround the pipe; and (b) a guide system extending along the length and adjacent to the surface of the pipe; the coil adapted to engage the guide system to provide for travel of the coil along the pipe.

Another aspect of the present invention is to provide a removable coil for an eddy current testing apparatus for nondestructive examination of a pipe. The coil includes a cable having a plurality of conductors adapted to form a continuous conductor coil when the cable is circumferentially wrapped around the pipe.

Still another aspect of the present invention is to provide an eddy current testing apparatus for nondestructive examination of pipe. The apparatus includes: (a) an eddy current coil adapted to removably circumferentially surround the pipe, the coil including a cable having a plurality of conductors adapted to form a continuous conductor coil when the cable is circumferentially wrapped around the pipe; (b) a guide system extending along the length and adjacent to the surface of the pipe; and (c) a coil form adapted to removably circumferentially surround the pipe and engage the guide system to provide for travel of the coil along the pipe.

These and other aspects of the present invention will become apparent to those skilled in the art after a reading of the following description of the preferred embodiment when considered with the drawings.

BRIEF DESCRIPTION OF THE DRAWINGS

FIG. 1 is a cross-sectional view of a nondestructive examination eddy current system constructed according to the present invention in use for inspecting an installed and/or insulated pipe;

FIG. 2A is a perspective view of an insulated pipe segment with guide rails attached constructed according to the present invention;

FIG. 2B is an end view of the insulated pipe segment with rectangular guide rails attached shown in FIG. 2A;

FIG. 2C is an end view of an alternative embodiment of the insulated pipe segment with tubular guide rails attached shown in FIG. 2A;

FIG. 8 is a end view of a wrapped encircling coil constructed according to the present invention;

FIG. 9 is a side view of a nondestructive examination eddy current system using a differential eddy current coil connection according to one embodiment of the present invention;

FIG. 10 is a side view of a nondestructive examination eddy current system using an absolute eddy current coil connection according to another embodiment of the present invention; and FIG. 11 is a cross-sectional view of an eddy current coil system similar to that shown in FIG. 1 further including rollers.

DESCRIPTION OF THE PREFERRED EMBODIMENTS

Figure 3A:
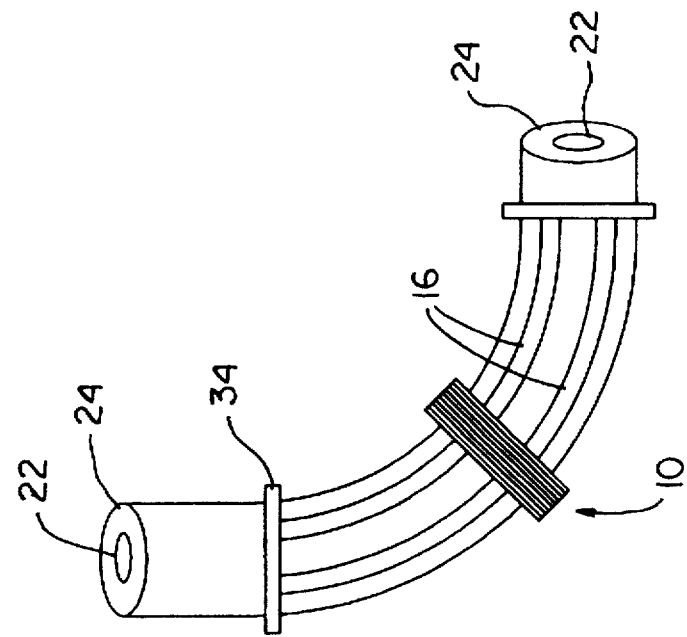
FIG. 3A is a side view of a nondestructive examination eddy current system for examining arcuate installed and/or insulated piping segments using coil guides constructed according to the present invention.

In the following description, like reference characters designate like or corresponding parts throughout the several views. Also in the following description, it is to be understood that such terms as "forward", "rearward", "left", "right", "upwardly", "downwardly", and the like are words of convenience and are not to be construed as limiting terms.

Referring now to the drawings in general and FIG. 1 in particular, it will be understood that the illustrations are for the purpose of describing a preferred embodiment of the invention and are not intended to limit the invention thereto. As best seen in FIG. 1, an NDE eddy current system, generally designated 10, is shown constructed according to the present invention. The NDE eddy current system 10 includes three major sub-assemblies: an encircling coil 12; a coil form 14; and guide rails 16.

As can be seen, the encircling coil 12 encircles the coil form 14 according to coil guides 20. The encircling coil 12 is connected to an eddy current measuring instrument 32 via connecting cables 30 and connectors 26. The encircling coil 12 and coil form 14 surround the outer surface of a pipe 22 encased with a layer of insulation 24. The coil form 14 is operatively associated with the guide rails 16 to facilitate axial movement along pipe 22.

Turning now to FIG. 2A, there is shown an insulated pipe 22 having insulation 24 with guide rails 16 mounted axially thereon. The guide rails 16 guide the path of movement of the coil form 14 during examination. Also shown are end views of the insulated pipe 22 wherein the guide rails 16 are rectangular, referenced 16a, or tubular, referenced 16b (FIGS. 2B and 2C). Those of ordinary skill in the art will recognize that the number of guide rails 16 and the spacing therebetween will vary from embodiment to embodiment.

As best seen in FIG. 3A, the guide rails 16 may be shaped according to the contours of the pipe 22 under examination. Preferably, rail brackets 34 are used to secure the guide rails 16 in place on the insulation 24. Preferably, the guide rails 16 are a set of thin rectangular rails installed on a top or side of the insulation 24 of pipe 22 to be examined. The guide rails 16 provide a smooth track for the coil form 14 and encircling coil 12 to travel. The guide rails 16 minimize any eddy current signal noise caused by coil liftoff variation or wobble movement during an examination scan.

Figure 3B:
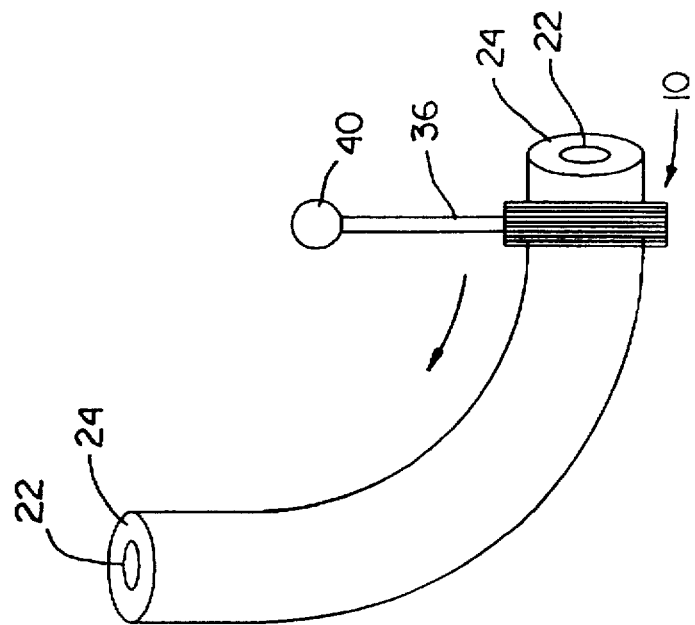
FIG. 3B is a side view of a nondestructive examination eddy current system for examining arcuate installed and/or insulated piping segments using a pivot fixture constructed according to the present invention.

FIG. 3B depicts an alternative embodiment for providing a smooth track for coil form 14 and encircling coil 12 travel. A pivot fixture 41 having a pivot arm 36 connected to the coil form 14 may be configured to provide an arcuate path of travel coinciding with the configuration or shape of pipe 22. The exact configuration of the guide rails 16 or movement fixture 41 will vary with the geometry of the pipe 22 under examination.

Figure 4A:
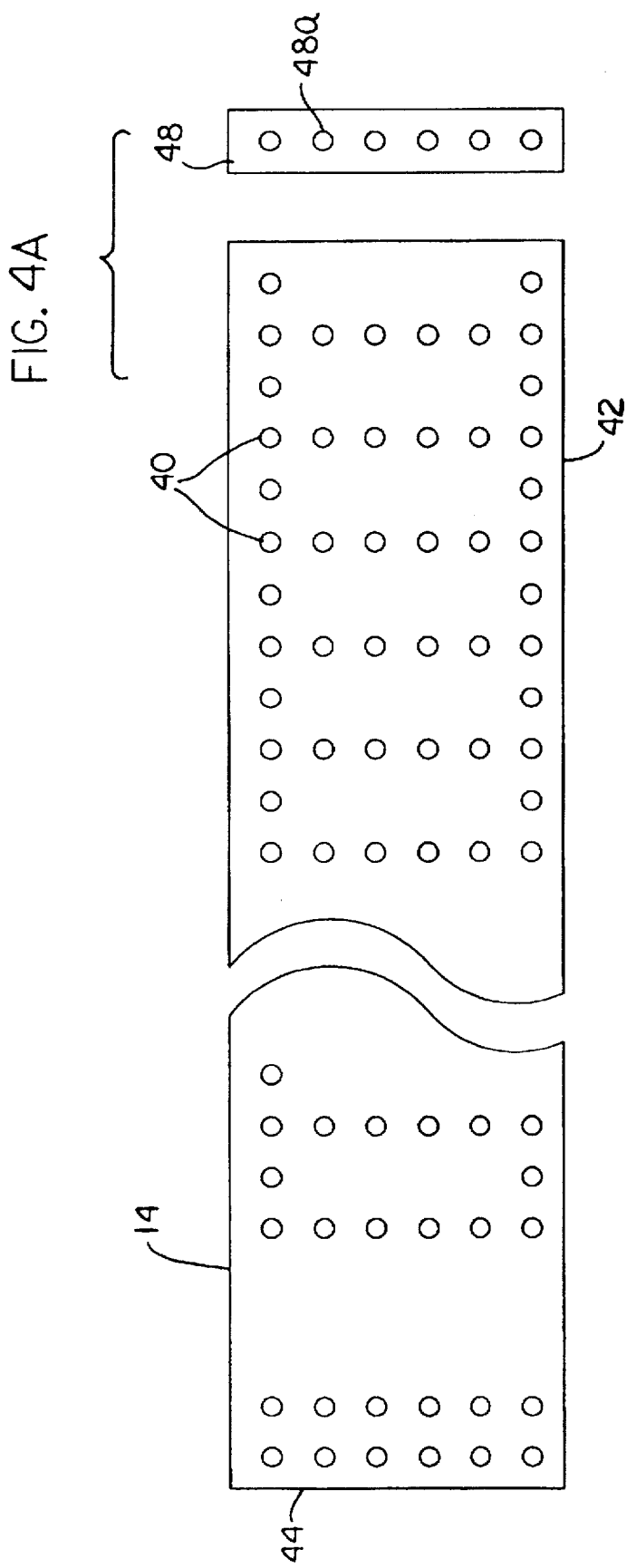
FIG. 4A is a side view of an unrolled coil form constructed according to the present invention.

As best seen in FIG. 4A, an open or unrolled coil form 14 is shown. The coil form 14 has multiple holes 40 drilled in a hole pattern to accept fasteners 48 and coil guides 20. Although many flexible materials may be used to make the coil form 14, preferably a flexible nylon or DELRIN strip is used (DELRIN is a registered trademark of E. I. dupont de Nemours and Company of Wilmington, Del.). The width of end 44 of coil form 14 will typically depend on the amount of coil separation, if two encircling coils 12 are used to form a differential eddy current measurement configuration, and whether perm material is required for focusing or shielding during examination. Suitable perm materials include ferromagnetic materials such as iron pole pieces and flexible strips containing iron.

The length of the side 42 of coil form 14 depends on the circumference of the insulated pipe 22. The side 42 of coil form 14 is long enough to wrap around the pipe 22 and provide sufficient clearance for smooth movement along the pipe 22 on guide rails 16. Alternatively, if a pivot fixture 40 is used instead of guide rails 16, guide rails 16 will not be a factor.

Figure 4B:
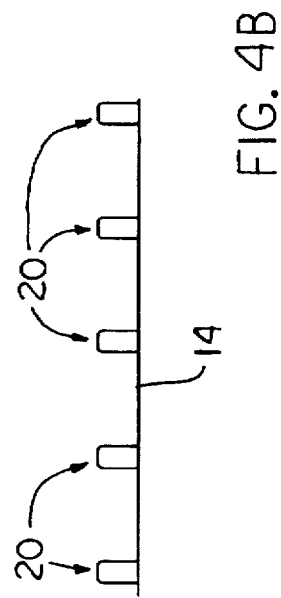
FIG. 4B is an end view of the unrolled coil form shown in FIG. 4A.

A side view of the unrolled coil form 14 is shown in FIG. 4B. Multiple coil guides 20 are inserted into holes 40 to help facilitate positioning and alignment of the encircling coil 12 when wrapped about coil form 14 after placement about pipe 22. To install the coil form 14 on the insulated pipe 22, the coil form 14 is wrapped around insulated pipe 22 and fasteners 48 connect the ends 44 of coil form 14 to form a semi-rigid cylindrical structure. As shown in FIG. 4A, the fastener 48 may have fastener post 48a to facilitate fastening.

Figure 4C:
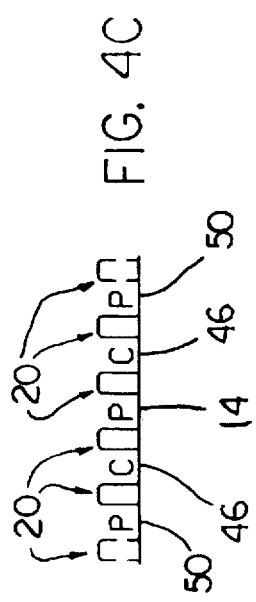
FIG. 4C is an end view the unrolled coil form shown in FIG. 4A.

In FIG. 4C, an end view of coil form 14 is shown. Multiple coil guides 20 are shown inserted in coil form 14 to form alternating perm slots 50 and coil slots 46. The encircling coil 12 will align in coil slots 46 while perm material, if required, will align perm slots 50.

Figure 5:
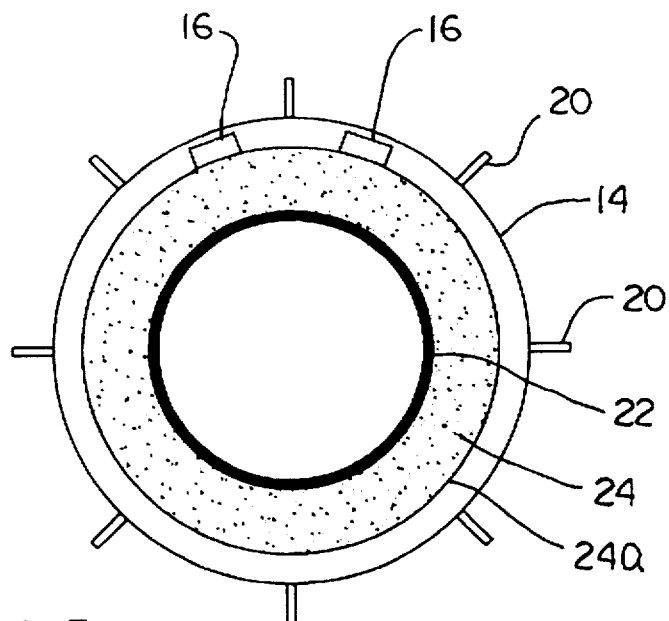
FIG. 5 is a cross-sectional view of the coil form shown in FIG. 1, without the coil.

FIG. 5 depicts a coil form 14 wrapped around the insulated pipe 22 without the encircling coil 12. The coil form 14 surrounds insulated pipe 22 and engages the guide rails 16.

Coil guides 20 provide guide posts for winding the encircling coil 12 about the coil form 14.

Figure 6:
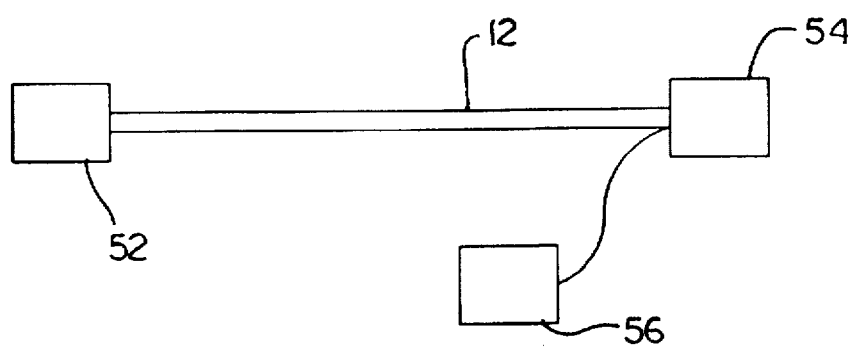
FIG. 6 is an schematic diagram of an unwrapped encircling coil constructed according to the present invention.

FIG. 6 depicts an encircling coil 12 in an unwrapped state. An encircling coil typically includes a male connector 52 and a female connector 54 configured to engage one another. Upon engagement, a continuous coil, further discussed below, is formed. An instrument connector 56 is provided to connect the encircling coil 12 to an eddy current instrument 32 (as shown in FIG. 1). Preferably, the length of the unwrapped encircling coil is 6 to 8 times the circumference of the insulated pipe 22. The encircling coil typically consists of 50 to 100 conductors 60 of 20 to 32 gauge copper magnet wire inside a heat shrink covering.

Figure 7:
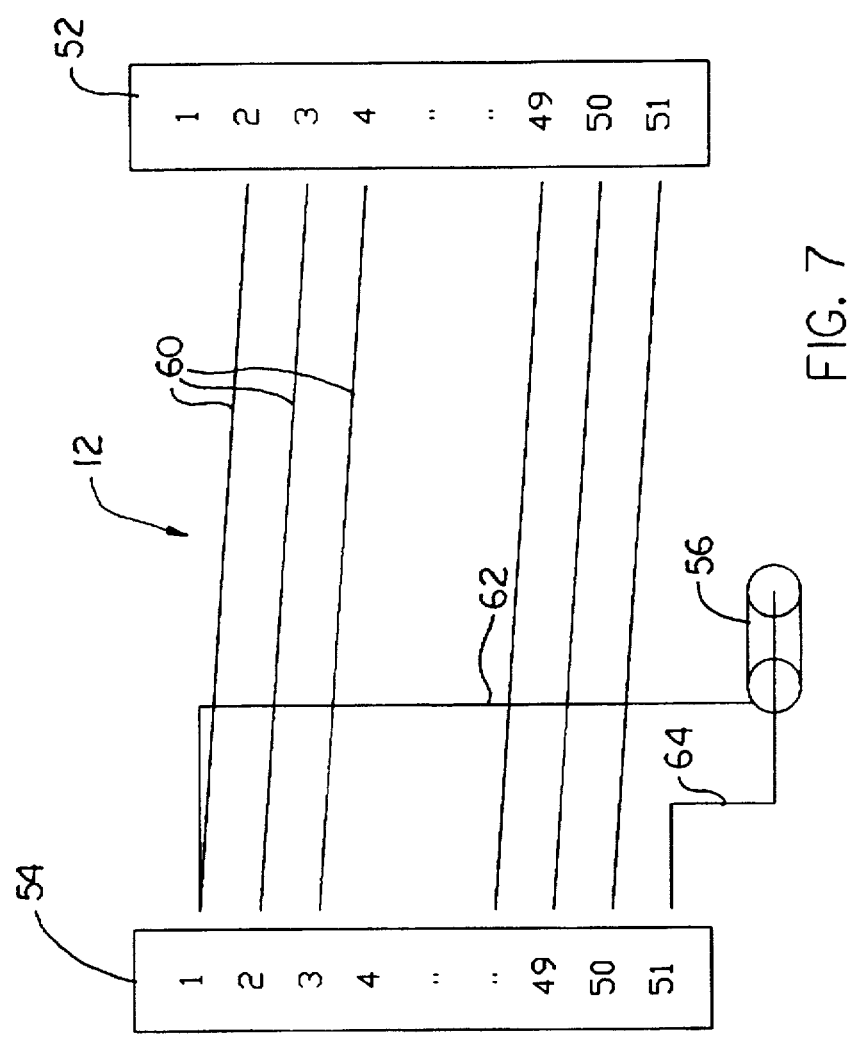
FIG. 7 is a coil wiring schematic for the encircling coil shown in FIG. 6.

As best seen in FIG. 7, the encircling coil 12 uses a unique wiring configuration to form a single, continuous conductor when the male and female connectors, 52, 54, are connected. In other words, the pin out of one connector is shifted one pin in the other such that when the connectors 52, 54 are connected, a continuous conductor is formed. The lengths of the conductors 60 are determined by the pipe 22 and insulation 24 diameter and the number of turns required for the coil sensitivity and proper frequency range required for the particular application. Additional connectors 62, 64 connect opposite ends of the encircling coil 12 to instrument connector 56 to facilitate connection to the eddy current instrument 32.

As best seen in FIG. 8, the encircling coil 12 is shown circumferentially connected at connectors 52, 54 to form a single loop of 50 conductors 60. As discussed above, the separate conductors 60 form a continuous coil. In the configuration shown, a single turn of the encircling coil 12 provides a five-turn eddy current coil. In the preferred embodiment, the encircling coil 12 is wrapped around the coil form 14 multiple times. For example, when the encircling coil 12 is wrapped around the coil form 14 six times, the resulting eddy current coil has 300 turns (6×50).

The capability to wrap a 300 turn eddy current coil around a pipe in a period of approximately 4 minutes is a tremendous improvement over the prior art and provides a unique feature with regard to the current invention. Increasing the number of conductors 60 to 100 would further reduce the number of wraps and installation time. Once one or more encircling coils 12 are wrapped in place on coil form 14, the connectors 52, 54 are connected together to complete the circuit and the encircling coil is secured in place. The coil form 14 provides structure and uniformity for each encircling coil 12.

Once the encircling coils 12 are connected about coil form 14, they may be connected to a standard reflective impedance (or driver pickup) eddy current instrument 32. After balancing the instrument 32, the coils are placed on one end of the region to be scanned.

Looking now at FIG. 9, the appropriate identification and location data is entered to clearly delineate the section under examination and then the eddy current data is recorded as the coil is moved slowly through the examination zone along the insulated pipe 22. FIG. 9 specifically depicts a differential coil pair wherein both encircling coils 12 are on the same coil form.

Alternatively, an absolute configuration is shown in FIG. 10. In an absolute configuration, a fixed coil system 68 is held fixed at one end of the examination area on insulated pipe 22. Another coil system 70 is initially spaced apart from the fixed coil system 68. During examination, the coil system 70 moves over the examination area towards the fixed coil system 68. Those of ordinary skill in the art will recognize the benefit of the different coil configurations.

As depicted in FIG. 11, a plurality of rollers 72 could be added to the coil form 14 to provide for smoother movement along the insulated pipe 14.

The overall speed of the eddy current encircling coil examination, as disclosed by the present invention, provides a significant speed advantage over the systems of prior art. The installation of the coil and the acquisition of data is much faster relative to the techniques of the prior art. Furthermore, the scan pattern is a single axial scan instead of a grid scan in two dimensions. Additionally, the encircling coil form and concept allow for use of material having a higher permeability around the windings to improve field focus. For example, flexible magnet material can be used in the areas between the coil windings and the outside coil windings to accomplish this field concentration. Thus, the applicants' invention provides an eddy current coil having a high detection sensitivity for wall loss pipe degradation.

The coil of the present invention is capable of operating in absolute and differential modes. The coil enables smooth scanning of a region of interest with minimal wobble or relative movement between two windings in a differential configuration. The coil form is structurally stable to provide high integrity during examination. The coil system accommodates pipe installations with different pipe diameters and insulation (or lagging) thicknesses. The coil system provides the ability to easily obtain enough turns of a necessary wire gauge to provide the required sensitivity and frequency range for the material and insulation thickness under examination. Lastly, the coil system provides a fast and easy NDE technique for operators.

Certain modifications and improvements will occur to those skilled in the art upon a reading of the foregoing description. By way of example, while in the preferred embodiment, the coil and coil form are flexible to accommodate various diameters of piping, semi-rigid coils and coil forms could be used for known pipe diameters. It should be understood that all such modifications and improvements have been deleted herein for the sake of conciseness and readability but are properly within the scope of the following claims.

We claim:

1. An eddy current testing apparatus for nondestructive examination of pipe, said apparatus comprising:

(a) an eddy current coil adapted to removably circumferentially surround said pipe;

(b) a guide system extending along the length and adjacent to the surface of said pipe; said coil adapted to engage said guide system to provide for travel of said coil along said pipe; and (c) a coil form having a flexible body with opposing ends adapted to removably circumferentially surround said pipe, provide form for said eddy current coil and engage said guide system to provide for travel of said coil along said pipe.

2. The apparatus according to claim 1, wherein said guide system includes a plurality of spaced apart rails.

3. The apparatus according to claim 2, wherein said guide system includes two of said rails and said rails are aligned substantially parallel along said pipe.

4. The apparatus according to claim 3, wherein said rails are generally rectangular.

5. The apparatus according to claim 2, wherein said rails are generally tubular.

6. The apparatus according to claim 2, wherein said guide system includes a rail bracket operatively attached to said rails to secure said rails to said pipe.

7. The apparatus according to claim 2, wherein said rails track the contours of said pipe.

8. The apparatus according to claim 2, wherein said rails are arcuately shaped to facilitate travel around bends in said pipe.

9. The apparatus according to claim 1, wherein said guide system includes a guide fixture apart from said pipe.

10. The apparatus according to claim 9, wherein said guide fixture includes a pivot arm adapted to engage said coil form and pivot about a pivot point; said pivot arm being adapted to provide an arcuate path of travel, along a bend in said pipe, for said coil.

11. The apparatus according to claim 1, wherein said coil form is made from a flexible strip having a body connected at opposing ends.

12. The apparatus according to claim 11, wherein said flexible strip further includes a connector at one of said ends; said connector being adapted to connect to said opposite end of said flexible strip or said body of said flexible strip via openings in said body.

13. The apparatus according to claim 12, wherein said coil form forms a substantially cylindrical body having a body adapted to receive said connector; said hole pattern providing for a plurality of coil form mounting sizes.

14. The apparatus according to claim 1, wherein said coil form is made of nylon.

15. The apparatus according to claim 1, wherein said coil form is formed from DELRIN.

16. The apparatus according to claim 1, wherein said coil form forms a substantially deformable cylindrical body.

17. The apparatus according to claim 1, wherein said cylindrical body of said coil form has a length sufficient for spaced apart placement of a plurality of eddy current coils thereon.

18. The apparatus according to claim 1, wherein said cylindrical body of said coil form includes perm material to facilitate eddy current focusing or shielding.

19. The apparatus according to claim 1, wherein said perm material is selected from the group consisting of ferromagnetic materials such as iron pole pieces and flexible strips containing iron.

20. The apparatus according to claim 1, wherein said cylindrical body of said coil form is adjustably adapted to surround pipes of varying size.

21. The apparatus according to claim 1, wherein said coil form forms a substantially cylindrical body including one or more coil guides for providing alignment of said coil.

22. The apparatus according to claim 21, wherein said cylindrical body of said coil form contains openings adapted to receive said coil guides.

23. An eddy current testing apparatus for nondestructive examination of pipe, said apparatus comprising:
(a) an eddy current coil adapted to removably circumferentially surround said pipe, said coil including a cable having a plurality of conductors adapted to form a continuous conductor coil when said cable is circumferentially wrapped around said pipe;
(b) a guide system extending along the length and adjacent to the surface of said pipe; and
(c) a circumferentially adjustable coil form having a flexible body with opposing ends adapted to removably circumferentially surround said pipe, provide a form for said eddy current coil and engage said guide system to provide for travel of said coil along said pipe on said guide system.

24. The apparatus according to claim 23, wherein said guide system includes a plurality of spaced apart rails.

25. The apparatus according to claim 24, wherein said guide system includes two of said rails and said rails are aligned substantially parallel along said pipe.

26. The apparatus according to claim 24, wherein said rails are generally rectangular.

27. The apparatus according to claim 24, wherein said rails are generally tubular.

28. The apparatus according to claim 24, wherein said guide system includes a rail bracket operatively attached to said rails to secure said rails to said pipe.

29. The apparatus according to claim 24, wherein said rails track the contours of said pipe.

30. The apparatus according to claim 24, wherein said rails are arcuately shaped to facilitate travel around bends in said pipe.

31. The apparatus according to claim 23, wherein said guide system includes a guide fixture apart from said pipe.

32. The apparatus according to claim 31, wherein said guide fixture includes a pivot arm adapted to engage said coil form and pivot about a pivot point; said pivot arm being adapted to provide an arcuate path of travel, along a bend in said pipe, for said coil.

33. The apparatus according to claim 23, wherein said coil form is made from a flexible strip having a body connected at opposing ends.

34. The apparatus according to claim 33, wherein said flexible strip further includes a connector at one of said ends; said connector being adapted to connect to said opposite end of said flexible strip or said body of said flexible strip via openings in said body.

35. The apparatus according to claim 34, wherein said coil form forms a deformable and substantially cylindrical body having a hole pattern adapted to receive said connector; said hole pattern providing for a plurality of coil form mounting sizes.

36. The apparatus according to claim 23, wherein said coil form is made of nylon.

37. The apparatus according to claim 23 wherein said coil form is formed from DELRIN.

38. The apparatus according to claim 23, wherein said coil form forms a deformable and substantially cylindrical body.

39. The apparatus according to claim 23, wherein said cable includes a sufficient number of said conductors to provide a desired eddy current coil frequency range when wrapped around said pipe.

40. The apparatus according to claim 23, wherein said cable includes at least five conductors.

41. The apparatus according to claim 23, wherein said cable includes at least fifty conductors.

42. The apparatus according to claim 23, wherein each of said plurality of conductors has two opposite ends; each said conductor end adapted to couple to an opposite end of another conductor in order to form said continuous conductor coil when said cable is circumferentially wrapped around said pipe.

43. The apparatus according to claim 23, wherein said cable provides for a plurality of wrappings of said cable around said pipe; said coil having an effective number of turns equal to the product of a number of said conductors and said wrappings.

44. The apparatus according to claim 43, wherein said cable provides for at least 6 wraps around said pipe.

45. The apparatus according to claim 23, wherein said cable has a first end with a first connector and a second end with a second connector adapted to mate with said first connector, each of said connectors have a plurality of conductor positions for receiving one said conductor, said conductor positions of said first connector being offset from said conductor positions in said second connector, wherein said conductors form said continuous conductor coil when said connectors mate.

46. The apparatus according to claim 23, wherein said cable includes a sufficient number of said conductors to provide a desired eddy current coil sensitivity when wrapped around said pipe.

47. The apparatus according to claim 23, wherein, said coil form forms a deformable and substantially cylindrical body having a length sufficient for spaced apart placement of a plurality of eddy current coils thereon.

48. The apparatus according to claim 23, wherein said coil form forms a deformable and substantially cylindrical body having perm material to facilitate eddy current focusing or shielding.

49. The apparatus according to claim 48, wherein said perm material is selected from the group consisting of ferromagnetic materials such as iron pole pieces and flexible strips containing iron.

50. The apparatus according to claim 23, wherein said coil form forms a deformable and substantially cylindrical body adjustably adapted to surround pipes of varying size.

51. The apparatus according to claim 23, wherein said coil form forms a deformable and substantially cylindrical body having one or more coil guides for providing alignment of said coil.

52. The apparatus according to claim 51 wherein said cylindrical body of said coil form contains openings adapted to receive said coil guides.

* * * * *